United States Patent [19]

Preiss

[11] Patent Number: 4,633,007

[45] Date of Patent: Dec. 30, 1986

[54] PREPARATION OF BENZYLIDENE COMPOUNDS

[75] Inventor: Michael Preiss, Wuppertal, Fed. Rep. of Germany

[73] Assignee: Bayer Aktiengesellschaft, Leverkusen, Fed. Rep. of Germany

[21] Appl. No.: 832,503

[22] Filed: Feb. 21, 1986

[30] Foreign Application Priority Data

Mar. 9, 1985 [DE] Fed. Rep. of Germany ....... 3508533

[51] Int. Cl.$^4$ .................. C07C 143/525; C07C 79/38; C07C 121/76; C07C 69/738
[52] U.S. Cl. ...................................... 560/014; 560/23; 560/51; 560/53; 558/357
[58] Field of Search ....................... 560/23, 14, 51, 53; 558/357

[56] References Cited

PUBLICATIONS

Fieser and Fieser, Reagents for Organic Synthesis, vol. 4 (1974) 507–508.
Jones, Organic Reactions, vol. 15 (1967) 204–205, 248–253, 472–475.

*Primary Examiner*—Bernard Helfin
*Attorney, Agent, or Firm*—Sprung Horn Kramer & Woods

[57] ABSTRACT

A process for the preparation of a benzylidene compound of the formula

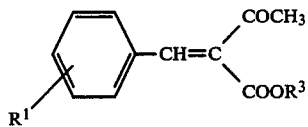

in which $R^1$ is hydrogen or one or two substituents independently selected from the group consisting of nitro, cyano, halogen, SO$_3$H, alkyl, alkoxy and fluorinated alkyl, each with 1 to 4 C atoms and two or three fluorine substituents, and $R^3$ is alkyl with 1 to 10 C atoms, which is optionally interrupted by an oxygen in the chain or is optionally substituted by fluorine, chlorine, hydroxyl or a methylbenzylamine group, comprising reacting an acetal of the formula

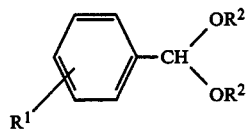

in which $R^2$ each independently is alkyl with 1 to 6 C atoms, which is optionally substituted by phenyl, or the two radicals $R^2$ conjointly form an alkylene radical with 1–6 C atoms, with a β-ketocarboxylic acid ester of the formula

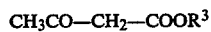

in the presence of an acid at a temperature between about 40° and 120°.

6 Claims, No Drawings

PREPARATION OF BENZYLIDENE COMPOUNDS

The present invention relates to a new process for the preparation of substituted benzylidene compounds from aromatic acetals and β-ketocarboxylic acid esters and to their use as intermediates in the preparation of biologically active substances.

Benzylidene compounds, their preparation and their use in the synthesis of pharmaceutically active dihydropyridines are already known (compare DE-OS (German Published Specification) No. 2,117,571 and DE-OS (German Published Specification) No. 2,117,573). The known processes of preparation are essentially based on a condensation of aldehydes with acetoacetic acid esters. The use of aldehydes is in many cases undesirable, especially in view of their possible toxicity and the associated health hazards in the process of preparation.

The present invention relates to a process for the preparation of benzylidene compounds of the general formula (I)

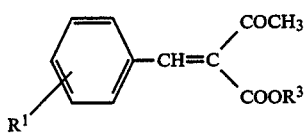

in which
$R^1$ represents hydrogen or one or two substituents from the group of nitro, cyano, halogen, $SO_3H$, alkyl, alkoxy and fluorinated alkyl, each with 1 to 4 C atoms and two or three fluorine substituents and $R^3$ represents alkyl with 1 to 10 C atoms, which is optionally interrupted by an oxygen in the chain or is optionally substituted by fluorine, chlorine, hydroxyl or a methylbenzylamino group,
characterized in that acetals of the general formula (II)

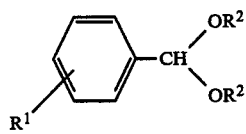

in which
each $R^2$ represents alkyl with 1 to 6 C atoms, which is optionally substituted by phenyl, or the two radicals $R^2$ conjointly represent an alkylene radical with 1–4 C atoms are condensed with β-ketocarboxylic acid esters of the general formula (III)

$$CH_3CO-CH_2-COOR^3 \quad \text{(III)}$$

in which
$R^3$ has the abovementioned meaning in the presence of an acid and, if appropriate, in the presence of an organic solvent, at temperatures between 40° and 120° C. and, if appropriate, in the presence of catalytic amounts of an amine.

Given a knowledge of the state of the art, it was not to be expected that the benzylidene compounds of the formula (I) could be prepared in such high purity and good yields directly from the acetals of the general formula (II), without isolation of the corresponding aldehydes.

The acetals of the general formula (II) which can be used according to the invention are known or can be prepared in accordance with known methods (compare DE-OS (German Published Specification) No. 3,212,069).

Acids which are preferably used are organic monocarboxylic and dicarboxylic acids, such as, for example, formic acid, acetic acid, propionic acid, oxalic acid, malonic acid, trifluoroacetic acid and lactic acid.

Preferred inert organic solvents which are used are lower alcohols with up to 10 carbon atoms, such as, for example, methanol, ethanol, propanol, isopropanol, butanol, hexanol, glycol, diglycol and triglycol; hydrocarbons with up to 10 C atoms, such as, for example, hexane, benzene, toluene and xylene, ethers, such as, for example, methoxyethanol, ethoxyethanol, butoxyethanol, 1,2-dimethoxyethane, glycol dimethyl ether, diglycol dimethyl ether and anisole.

As catalytically active amines there may preferentially be mentioned piperidine, pyrimidine, pyridine, pyridazine, piperazine and morpholine.

The amines are generally employed in about 0.001 to 0.30 and preferably about 0.01 to 0.10 moles per mole of acetal.

The process according to the invention is preferably carried out at temperatures between 40° and 120°, especially between 60° and 110° C.

The examples which follow illustrate the process according to the invention.

EXEMPLARY EMBODIMENTS

EXAMPLE 1

98.5 parts by weight of o-nitrobenzaldehyde dimethylacetal and 63.8 parts by weight of methyl acetoacetate as well as 10 parts by volume of piperidine are dissolved in 325 parts by volume of glacial acetic acid and the mixture is warmed overnight to 80° C. The volatile constituents are stripped off and the residue is taken up in isopropanol. Hereupon, methyl 2-(2-nitrobenzylidene)-acetoacetate crystallizes out after a short time (melting point 97°–99° C.). The yield is 86% of theory.

EXAMPLE 2

This is carried out as in Example 1, but with formic acid instead of glacial acetic acid. The yield is 84%.

EXAMPLE 3

This is carried out as in Example 1, except with propionic acid instead of glacial acetic acid, at 110° C. The yield is 37%.

EXAMPLE 4

98.5 parts by weight of o-nitrobenzaldehyde dimethylacetal and 63.8 parts by weight of methyl acetoacetate as well as 2 parts by volume of piperidine are dissolved in 163 parts by volume of toluene and 163 parts by volume of formic acid and the mixture is warmed overnight to 80° C. The volatile constituents are stripped off and the residue is treated as in Example 1. The yield is 83%.

EXAMPLE 5

This is carried out as in Example 4, except that isopropanol/formic acid is used in place of toluene/formic acid and the mixture is kept at the reflux temperature. The yield is 61%.

EXAMPLE 6

98.5 parts by weight of o-nitrobenzaldehyde dimethylacetal and 63.8 parts by weight of methyl acetoacetate as well as 10 parts by volume of piperidine are dissolved in 263 parts by volume of toluene and 50 parts by weight of chloroacetic acid and the mixture is warmed overnight to 80° C. The volatile constituents are stripped off and the residue is treated as in Example 1. The yield is 33%.

EXAMPLE 7

This is carried out as in Example 6, except that 50 parts by weight of malonic acid are employed in place of chloroacetic acid. The yield is 24%.

It is understood that the specification and examples are illustrative but not limitative of the present invention and that other embodiments within the spirit and scope of the invention will suggest themselves to those skilled in the art.

I claim:

1. A process for the preparation of a benzylidene compound of the formula

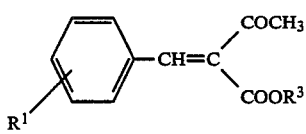

in which
R$^1$ is hydrogen or one or two substituents independently selected from the group consisting of nitro, cyano, halogen, SO$_3$H, alkyl, alkoxy and fluorinated alkyl, each with 1 to 4 C atoms and two or three fluorine substituents, and
R$^3$ is alkyl with 1 to 10 C atoms, which is optionally interrupted by an oxygen in the chain or is optionally substituted by fluorine, chlorine, hydroxyl or a methylbenzylamine group, comprising reacting an acetal of the formula

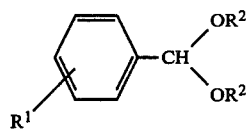

in which
R$^2$ each independently is alkyl with 1 to 6 C atoms, which is optionally substituted by phenyl, or the two radicals R$^2$ conjointly form an alkylene radical with 1–4 C atoms, with a β-ketocarboxylic acid ester of the formula $$CH_3CO—CH_2—COOR^3$$

in the presence of an acid at a temperature between about 40° and 120°.

2. The process according to claim 1, wherein the acid is an organic carboxylic acid.

3. The process according to claim 1, wherein the reaction is effected in the presence of a catalyst selected from the group consisting of piperidine, pyrimidine, pyridine, pyridazine, piperazine, morpholine, and mixtures thereof whereby the amount of the catalyst is 0.001–0.30 moles per mole of acetale.

4. The process according to claim 1, wherein the reaction is effected in the presence of a solvent selected from the group consisting of a lower alcohol, hydrocarbon or ether with up to 10 carbon atoms and mixtures thereof.

5. The process according to claim 1, wherein the reaction is carried out at a temperature between 60° and 110° C.

6. The process according to claim 2, wherein the reaction is carried out at a temperature between 60° and 110° C., in the presence of a catalyst selected from the group consisting of piperidine, pyrimidine, pyridine, pyridazine, piperazine, morpholine, and mixtures thereof, and in the presence of a solvent selected from the group consisting of a lower alcohol, hydrocarbon or ether with up to 10 carbon atoms and mixtures thereof.

* * * * *